US007223535B2

(12) United States Patent
Fields et al.

(10) Patent No.: US 7,223,535 B2
(45) Date of Patent: *May 29, 2007

(54) SYNTHETIC PEPTIDES IMMUNOREACTIVE WITH HEPATITIS A VIRUS ANTIBODIES

(75) Inventors: Howard A. Fields, Marietta, GA (US); Yury E. Khudyakov, Duluth, GA (US)

(73) Assignee: Centers for Disease Control, Atlanta, GA (US)

( * ) Notice: Subject to any disclaimer, the term of this patent is extended or adjusted under 35 U.S.C. 154(b) by 421 days.

This patent is subject to a terminal disclaimer.

(21) Appl. No.: 10/738,443

(22) Filed: Dec. 16, 2003

(65) Prior Publication Data

US 2004/0229214 A1    Nov. 18, 2004

Related U.S. Application Data

(63) Continuation of application No. 10/031,088, filed as application No. PCT/US00/19267 on Jul. 14, 2000, now abandoned, and a continuation-in-part of application No. 09/171,432, filed as application No. PCT/US97/06891 on Apr. 18, 1997, now Pat. No. 6,838,237.

(60) Provisional application No. 60/144,412, filed on Jul. 15, 1999, provisional application No. 60/015,644, filed on Apr. 19, 1996.

(51) Int. Cl.
*C12Q 1/70* (2006.01)
*C12P 15/00* (2006.01)

(52) U.S. Cl. .......................................... 435/5; 435/69.1
(58) Field of Classification Search .................. None
See application file for complete search history.

(56) References Cited

U.S. PATENT DOCUMENTS

| 4,391,904 A | 7/1983 | Litman et al. ................. 435/7 |
| 4,683,202 A | 7/1987 | Mullis ........................ 435/91 |
| 5,426,039 A | 6/1995 | Wallace et al. ............ 435/91.2 |
| 6,838,237 B2 * | 1/2005 | Fields et al. .................. 435/5 |

FOREIGN PATENT DOCUMENTS

| WO | WO 89/06658 | 7/1989 |
| WO | WO 97/40147 | 10/1997 |

OTHER PUBLICATIONS

Barringer et al., "Blunt-end and single-strand ligations by *Escherichia coli* ligase: influence on an in vitro amplication scheme,"*Gene* 89:117-122 (1990).
Beaucage and Caruthers, "Deoxynucleoside Phosphoramidites—A New Class of Key Intermediates for Deoxypolynucleotide Synthesis," *Tetrahedron Letts.* 22(20):1859-1862 (1981).
Chang et al., "Antigenic Heterogeneity of the Hepatitis C Virus NS4 Protein as Modeled with Synthetic Peptides," *Virology* 257:177-190 (1999).
Gillam and Smith, "Site-Specific Mutagenesis Using Synthetic Oligodeoxyribonucleotide Primers: I. Optimum Conditions and minimum Oligodeoxyribonucleotide Length," *Gene* 8:81-97 (1979).
Guatelli et al., "Isothermal, in vitro amplification of nucleic acids by a multienzyme reaction modeled after retroviral replication," *Proc. Natl. Acad. Sci. USA* 87:1874-1878 (Mar. 1990).
Jia et al., "Host Antibody Response to Viral Structural and Nonstructural Proteins after Hepatitis A Virus Infection," *J. Infect. Diseases* 165:273-280 (1992).
Khudyakov et al., "Antigenic Epitopes of the Hepatitis A Virus Polyprotein," *Virology* 260(2):260-272 (1999).
Kusov et al., "Synthetic peptide 62-75 VP3 of hepatitis A virus induces virus-binding antibodies," *Vopr. Virusol.* 36(2):114-117 (1991) (Abstract).
Kwoh et al., "Transcription-based amplification system and detection of amplified human immunodeficiency virus type 1 with a bead-based sandwich hybridization format," *Proc. Natl. Acad. Sci. USA* 86:1173-1177 (Feb. 1989).
Landegren et al., "A Ligase-Mediated Gene Detection Technique," *Science* 241:1077-1080 (Aug. 26, 1988).
Langer, "New Methods of Drug Delivery," *Science* 249:1527-1533 (Sep. 28, 1990).
Lomeli et al., "Quantitative Assays Based on the Use of Replicatable Hybridization Probes," *Clin. Chem.* 35(9):1826-1831 (1989).
Maxam and Gilbert, "Sequencing End-Labeled DNA with Base-Specific Chemical Cleavages," *Methods Enzymol.* 65(1):499-560 (1980).
Merrifield, "Solid Phase Peptide Synthesis. I. The Synthesis of a Tetrapeptide," *J. Am. Chem. Soc.* 85:2149-2154 (Jul. 20, 1963).
Needham-VanDevanter et al., "Characterization of an adduct between CC-1065 and a defined oligodeoxynucleotide duplex," *Nucl. Acid. Res.* 12(15):6159-6168 (1984).
Needleman and Wunsch, "A General Method Applicable to the Search for Similarities in the Amino Acid Sequence of Two Proteins," *J. Mol. Biol.* 48:443-453 (1970).

(Continued)

*Primary Examiner*—Bruce R. Campell
*Assistant Examiner*—Michelle Horning
(74) *Attorney, Agent, or Firm*—Needle & Rosenberg PC

(57) ABSTRACT

Synthetic peptides immunoreactive with hepatitis A virus (HAV) antibodies are provided. The peptides are useful as laboratory reagents to detect or quantify HAV antibodies in biological samples in clinical or research-based assays and for inducing an immune response to HAV when administered to a human or animal. The peptides contain antigenic epitopes, modified antigenic epitopes or combinations of epitopes of the major structural capsid polypeptides or non-structural polypeptides of HAV and contain one or more molecules of the amino acid glutamine (Q) at the carboxyl end of the peptide, which enhances immunoreactivity and immunogenicity, particularly IgM antibody reactivity.

7 Claims, No Drawings

OTHER PUBLICATIONS

Pearson and Regnier, "High-Performance Anion-Exchange Chromatography of Oligonucleotides," *J. Chrom.* 255:137-149 (1983).

Pearson and Lipman, "Improved tools for biological sequence comparison," *Proc. Natl. Acad. Sci. USA* 85:2444-2448 (Apr. 1988).

Ping et al., "Antigenic Structure of Human Hepatitis A Virus Defined by Analysis of Escape Mutants Selected against Murine Monoclonal Antibodies," *J. Virol.* 66(4):2208-2216 (1992).

Roberts et al., "Generation of an antibody with enhanced affinity and specificity for its antigen by protein engineering," *Nature* 328:731-734 (Aug. 20, 1987).

Robertson et al., "Antibody Response to Nonstructural Proteins of Hepatitis A Virus Following Infection," *J. Med. Virol.* 40:76-82 (1993).

Robertson et al., "Serological approaches to distinguish immune response to hepatitis A vaccine and natural infection," *Vaccine* 10(Supp. 1):S106-S109 (1992).

Smith and Waterman, "Comparison of Biosequences," *Adv. Appl. Math.* 2:482-489 (1981).

Sooknanan and Malek, "NASBA: A detection and amplification system uniquely suited for RNA," *Biotechnology* 13:563-564 (Jun. 1995).

Van Brunt, "Amplifying Genes: PCR and Its Alternatives," *Bio/Technology* 8:291-294 (Apr. 1990).

Wolff et al., "Direct Gene Transfer into Mouse Muscle in Vivo," *Science* 247:1465-1468 (Mar. 1990).

Wu and Wallace, "The Ligation Amplification Reaction (LAR)—Amplification of Specific DNA Sequences Using Sequential Rounds of Template-Dependent Ligation," *Genomics* 4:560-569 (1989).

* cited by examiner

SYNTHETIC PEPTIDES IMMUNOREACTIVE WITH HEPATITIS A VIRUS ANTIBODIES

CROSS REFERENCE TO RELATED APPLICATIONS

The present application is (1) a continuation of U.S. application Ser. No. 10/031,088, filed Jan. 14, 2002 now abandoned, which is the National Stage of International Application No. PCT/US00/19267, filed Jul. 14, 2000, which claims priority to U.S. Provisional Application No. 60/144,412, filed Jul. 15, 1999, and (2) a continuation-in-part of U.S. application Ser. No. 09/171,432, filed Nov. 23, 1998 now U.S. Pat. No. 6,838,237, which is the National Stage of International Application No. PCT/US97/06891, filed Apr. 18, 1997, which claims priority to U.S. Provisional Application No. 60/015,644, filed Apr. 19, 1996, which applications are incorporated by reference in their entireties.

This invention was made by the Centers for Disease Control and Prevention, an agency of the United States Government.

BACKGROUND OF THE INVENTION

Hepatitis A virus (HAV) is a morphologically, biochemically and immunologically distinct agent which produces infectious hepatitis A in humans after an incubation period of approximately two to six weeks. Hepatitis A is a liver disease which, although not commonly fatal, can induce long periods of debilitating illness. An estimated 1.4 million cases of hepatitis A are reported annually worldwide. The disease is commonly spread by direct contact with an infected individual or by HAV-contaminated drinking water and/or food.

HAV has been characterized as a unique member of the Picornaviridae family belonging to the enterovirus group. Like other picornaviruses, HAV contains a single-stranded, positive-strand infectious RNA genome encoding a single polyprotein, which is subsequently processed into structural and nonstructural proteins.

The following four major structural capsid polypeptides of the HAV polyprotein have been described and their approximate molecular weights have been determined as follows: VP1, 30,000 to 33,000 daltons (amino acids 492–791); VP2, 24,000 to 25,000 daltons, (amino acids 24–245); VP3, 21,000 to 27,000 daltons (amino acids 246–491); and VP4, 7,000 to 14,000 daltons (amino acids 1–23).

Four major non-structural proteins have also been identified and have been designated P2A (amino acids 792–980), P2B (amino acids 981–1087), P2C (amino acids 1088–1422), P3A (amino acids 1423–1496), P3B (amino acids 1497-1519) and P3C (amino acids 1520–1738). Only one serotype appears to exist, and significant antigenic variation has not been recognized among different HAV strains.

HAV infection is typically diagnosed by the detection of IgM or IgG antibodies to the capsid proteins. Currently available recombinant proteins or synthetic peptides have not successfully been used as alternate sources of antigen in an enzyme immunoassay (EIA) format for the detection of anti-HAV, a serum marker of infection. This lack of success has been attributed to poor antigenic reactivity of the recombinant protein due to the strict conformational nature of the naturally occurring HAV antigenic epitopes. For more than 15 years, the only available source of immunoreactive proteins was from HAV cell cultures. In fact, inactivated cell culture-derived HAV is currently used by all commercial companies who manufacture anti-HAV tests. Unfortunately, HAV is made in very small quantities in cell culture, has a limited animal host range, and is difficult to purify from infected cell cultures and animal tissues. In addition to the inconvenience and cost associated with the production, purification, and standardization of cell culture-derived HAV antigen, current commercially available assays are unable to discriminate between natural infections and vaccine induced immunity as emphasized in several publications (See, e.g., Jia et al., *J. Infect. Diseases* 165:273-280 (1992); Robertson et al., *Vaccine* 10(Supp. 1):106–109 (1992); and Robertson et al., *J. Med. Virol.* 40:76–82 (1993)). These tests utilize intact HAV, and therefore indiscriminately detect both natural and vaccine induced immune responses.

New concepts enabling the design of efficient and inexpensive synthetic diagnostic reagents, which can be used for the development of reliable anti-HAV diagnostic tests, are necessary. As such, there remains a need in the art for synthetic peptides which can be used as alternate sources of antigen in an enzyme immunoassay (EIA) format for the detection of anti-HAV. The present invention remedies such a need.

SUMMARY OF THE INVENTION

In one aspect, the present invention provides synthetic peptides that are immunoreactive with HAV antibodies. The peptides are useful as laboratory reagents to detect or quantify HAV antibodies in biological samples in clinical or research-based assays. The peptides are also useful for inducing an immune response to HAV when administered to a human or animal. The peptides contain antigenic epitopes, modified antigenic epitopes or combinations of epitopes of the major structural capsid polypeptides or non-structural polypeptides of HAV and contain one or more molecules of the amino acid glutamine (Q) at the carboxyl end of the peptide. The synthetic peptides generally have a length of from 9 to 35 amino acids and are synthesized using known chemical peptide synthesis techniques. It has been surprisingly discovered that the presence of the amino acid glutamine (Q) at the carboxyl end of the peptide enhances IgM antibody reactivity.

In one embodiment, the synthetic peptide includes an amino acid sequence that contains a Q amino acid residue at the C-terminal and both an antigenic portion of the amino acid sequence of the VP4 protein of the HAV polyprotein and an antigenic portion of the amino acid sequence of the VP2 protein of the HAV polyprotein. This synthetic peptide includes one or more of the amino acid sequences of SEQ ID NOS:1–10 and conservative variations thereof, or binds to an antibody specifically immunoreactive with one or more peptides having the amino acid sequences of SEQ ID NOS:1–10 and conservative variations thereof.

In another embodiment, the synthetic peptide includes an amino acid sequence that is substantially similar to an antigenic portion of the VP3 protein of the HAV polyprotein and contains a Q amino acid residue at the C-terminal of the peptide. This synthetic peptide includes one or more of the amino acid sequences of SEQ ID NOS:11–22 and conservative variations thereof, or binds to an antibody specifically immunoreactive with one or more peptides having the amino acid sequences of SEQ ID NOS:11–22 and conservative variations thereof.

In another embodiment, the synthetic peptide includes an amino acid sequence that is substantially similar to an antigenic portion of the VP1 protein of the HAV polyprotein and contains a Q amino acid residue at the C-terminal of the peptide. This synthetic peptide includes one or more of the amino acid sequences of SEQ ID NOS:23–38 and conservative variations thereof, or binds to an antibody specifically immunoreactive with one or more peptides having the amino acid sequences of SEQ ID NOS:23–38 and conservative variations thereof.

In a further embodiment, the synthetic peptide includes an amino acid sequence that is substantially similar to an antigenic portion of the P2A protein of the HAV polyprotein and contains a Q amino acid residue at the C-terminal of the peptide. This synthetic peptide includes one or more of the amino acid sequences of SEQ ID NOS:39–48 and conservative variations thereof, or binds to an antibody specifically immunoreactive with one or more peptides having the amino acid sequences of SEQ ID NOS:39–48 and conservative variations thereof.

In another embodiment, the synthetic peptide includes an amino acid sequence that is substantially similar to an antigenic portion of the P2B protein of the HAV polyprotein and contains a Q amino acid residue at the C-terminal of the peptide. This synthetic peptide includes the amino acid sequence of SEQ ID NO:49 and conservative variations thereof, or binds to an antibody specifically immunoreactive with a peptide having the amino acid sequence of SEQ ID NO:49 and conservative variations thereof.

In yet another embodiment, the synthetic peptide includes an amino acid sequence that is substantially similar to an antigenic portion of the P2C protein of the HAV polyprotein and contains a Q amino acid residue at the C-terminal of the peptide. This synthetic peptide includes one or more of the amino acid sequences of SEQ ID NOS:50–61 and conservative variations thereof, or binds to an antibody specifically immunoreactive with one or more peptides having the amino acid sequences of SEQ ID NOS:50–61 and conservative variations thereof.

In a further embodiment, the synthetic peptide includes an amino acid sequence that is substantially similar to an antigenic portion of the P3A protein of the HAV polyprotein and contains a Q amino acid residue at the C-terminal of the peptide. This synthetic peptide includes one or more of the amino acid sequences of SEQ ID NOS:62–65 and conservative variations thereof, or binds to an antibody specifically immunoreactive with one or more peptides having the amino acid sequences of SEQ ID NOS:62–65 and conservative variations thereof.

In yet a further embodiment, the synthetic peptide includes an amino acid sequence substantially similar to an antigenic portion of the P3B protein of the HAV polyprotein and contains a Q amino acid residue at the C-terminal of the peptide. This synthetic peptide includes the amino acid sequence of SEQ ID NO:66 and conservative variations thereof, or binds to an antibody specifically immunoreactive with a peptide having the amino acid sequence of SEQ ID NO:66 and conservative variations thereof.

In yet another embodiment, the synthetic peptide includes an amino acid sequence which is substantially similar to an antigenic portion of the P3C protein of the HAV polyprotein and contains a Q amino acid residue at the C-terminal of the peptide. This synthetic peptide includes one or more of the amino acid sequences of SEQ ID NOS:67–72 and conservative variations thereof, or binds to an antibody specifically immunoreactive with one or more peptides having the amino acid sequences of SEQ ID NOS:67–72 and conservative variations thereof.

More preferably, the synthetic peptide includes one or more of the amino acid sequences of SEQ ID NOS:7, 8, 12, 16, 46, 72, 86, 87 and conservative variations thereof, or binds to an antibody specifically immunoreactive with one or more peptides having the amino acid sequences of SEQ ID NOS:7, 8, 12, 16, 46, 72, 86, or 87 and conservative variations thereof.

Most preferably, the synthetic peptide includes the amino acid sequence of SEQ ID NO:47 or binds to an antibody specifically immunoreactive with a peptide having the amino acid sequence of SEQ ID NO:47.

A method of detecting or measuring anti-HAV antibodies in a biological sample or specimen is provided. In accordance with the method, one or more of the synthetic peptides provided herein is combined with the sample or specimen and the formation of complexes between the peptide and anti-HAV antibodies in the sample or specimen are detected or measured.

A method of making an antibody against HAV is also provided. The method comprises administering one or more of the peptides described herein to a human or animal, preferably a mammal.

Furthermore, a method is provided for differentiating between vaccine-induced immunity and natural HAV immunity. The method comprises contacting an isolated, nonstructural, immunogenic HAV peptide of the present invention with antibodies from mammalian serum; and detecting the formation of complexes between the immunogenic peptide and the antibodies, wherein the presence of peptide-antibody complexes indicates natural HAV immunity. Examples of suitable nonstructural immunogenic peptides suitable for use in this method of the present invention include, but are not limited to, peptides comprising an amino acid sequence selected from the group consisting of SEQ ID NOS:39–88 and conservative variations thereof.

In another aspect, isolated nucleic acid sequences encoding a synthetic peptide having an amino acid sequence selected from the group consisting of SEQ ID NOS:1–88 and conservative variations thereof are provided.

In a further aspect, a diagnostic kit is provided for the detection of HAV in a biological sample. The kit includes one or more of the synthetic peptides described herein. Preferably, the kit further includes a container in which the peptides and sample are combined, instructional materials, and reagents for binding the peptides to antibodies in the biological sample to form an antibody-antigen complex and reagents for detecting the complex.

In addition, immunogenic compositions containing a pharmaceutically acceptable carrier and one or more of the synthetic peptides described herein, in an amount sufficient to induce an immune response to HAV in a mammal, is also provided. Induction of an immune response is achieved when antibodies to HAV are produced. In a preferred embodiment, the immunogenic peptide is covalently attached, or conjugated, to a carrier protein. Suitable carriers include, but are not limited to, serum albumin, keyhole limpet hemocyanin, diphtheria toxin, tetanus toxin and synthetic polymers (e.g., poly(D-Leu:D-Glu)). As such, the immunogenic composition also provides immunogenic conjugates in which a carrier protein is covalently attached to a synthetic peptide.

Also provided herein is a method of inducing an immune response to HAV in a human or animal, preferably a mammal. In accordance with the method an immunologically effective amount of a pharmaceutical composition containing a pharmaceutically acceptable carrier and one or more of the synthetic peptides described herein is administered to a human or animal. The induction of an immune response is measured by the production of anti-HAV antibodies.

Other features, objects and advantages of the invention and its preferred embodiments will become apparent from the detailed description which follows.

DETAILED DESCRIPTION OF THE INVENTION

The present invention provides synthetic peptides that are immunoreactive with HAV antibodies and immunogenic when administered to a human or animal. The peptides are useful as laboratory reagents to detect or quantify HAV antibodies in biological samples in clinical or research-based assays and are also useful for inducing an immune response in a patient or subject for therapeutic or prophylactic purposes.

It has been unexpectedly discovered that the presence of the amino acid glutamine (Q) at the carboxyl end of a peptide enhances immunoreactivity and immunogenicity, particularly IgM antibody reactivity. Therefore, the present invention provides for synthetic peptides, having one or more glutamines at the carboxyl end of the peptide, that are reactive with HAV antibodies. The synthetic peptides provided herein contain antigenic epitopes, modified antigenic epitopes or combinations of antigenic epitopes of the major structural capsid polypeptides or non-structural polypeptides of HAV and further include one or more molecules of the amino acid glutamine (Q) at the carboxyl end of the peptide. The synthetic peptides generally have a length of from 9 to 35 amino acids and are synthesized using known chemical peptide synthesis techniques. Preferred synthetic peptides of the invention contain one glutamine residue at the carboxyl terminus of the peptide.

In addition, immunogenic compositions, such as vaccines, that contain the synthetic peptides are also provided. The compositions contain one or more of the synthetic peptides described herein and a pharmaceutical carrier or vehicle. In a vaccine composition, the synthetic peptide is preferably linked to a suitable carrier molecule.

Definitions

"Peptides," "polypeptides" and "oligopeptides" are chains of amino acids (typically L-amino acids) in which carbons are linked through peptide bonds formed by a condensation reaction between the carboxyl group of the carbon of one amino acid and the amino group of the carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free amino group on the amino acid at the amino terminal of the peptide, or to the amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction of the carboxy terminal of the peptide. Thus, when one amino acid is said to "follow" another, that amino acid is position closer to the carboxy terminal of the peptide than the "preceding" amino acid.

The term "residue" is used herein to refer to an amino acid (D or L) or an amino acid mimetic that is incorporated into an oligopeptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the immunogenic HAV peptides to which the phrase refers. Thus, the description of a peptide "consisting essentially of . . . " excludes any amino acid substitutions, additions, or deletions that would substantially alter the biological activity of that peptide.

"Antigen" refers to an entity or fragment thereof which can induce an immune response in a mammal. The term includes immunogens and regions responsible for antigenicity or antigenic determinants.

"Antigenic determinant" refers to a region of an HAV protein recognized by an antibody, e.g., in serum raised against wild-type HAV.

The phrases "specifically binds to a peptide" or "specifically immunoreactive with," when referring to an antibody, refers to a binding reaction which is determinative of the presence of the peptide, or an antibody to the peptide, in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity.

"Nucleic acid," as used herein, refers to a deoxyribonucleotide (DNA) or ribonucleotide (RNA) in either single- or double-stranded form, and unless otherwise limited, encompasses known analogs of natural nucleotides which can function in a manner similar to the naturally occurring nucleotides.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or sequences which may be introduced to provide codon preference in a specific host cell.

"Conservatively modified variations" of a particular sequence refers to amino acids encoded by nucleic acids which encode identical or essentially identical amino acid sequences, or, where the nucleic acid does not encode an amino acid sequence, to essentially identical sequences.

Because of the degeneracy of the genetic code, a large number of functionally identical nucleic acids encode any given peptide. Such nucleic acid variations are silent variations, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. (U.S.A.)* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" means that a polypeptide comprises a sequence that has at least 80% sequence identity, preferably 90%, more preferably 95% or more, compared to a reference sequence over a comparison window of about 10 to about 20. Another indication that polypeptide sequences are substantially identical is if one peptide is immunologically reactive with antibodies raised against the other peptide. Thus, the peptides of the invention include peptides immunologically reactive with antibodies raised against the disclosed immunogenic HAV peptides.

Various embodiments of synthetic peptides containing immunogenic epitopes of HAV and a Q residue at the C-terminal of the peptide are provided. In one embodiment, the synthetic peptide includes an amino acid sequence that contains a Q amino acid residue at the C-terminal and both an antigenic portion of the amino acid sequence of the VP4 protein of the HAV polyprotein and an antigenic portion of the amino acid sequence of the VP2 protein of the HAV polyprotein. This synthetic peptide includes one or more of the amino acid sequences of SEQ ID NOS:1–10 and conservative variations thereof, or binds to an antibody specifically immunoreactive with one or more peptides having the amino acid sequences of SEQ ID NOS:1–10 and conservative variations thereof. These sequences, their laboratory designations, and the corresponding SEQ ID NOS are as follows:

| | | |
|---|---|---|
| GLDHILSLADIEEEQMIQSVQ | (YK-1206), | (SEQ ID NO:1); |
| DRTAVTGASYFTSVDQSSVHQ | (YK-1208), | (SEQ ID NO:2); |
| EVGSHQVEPLRTSVDKPGSKQ | (YK-1210), | (SEQ ID NO:3); |
| EPLRTSVDKPGSKKTQGEKFQ | (YK-1211), | (SEQ ID NO:4); |
| DKPGSKKTQGEKFFLIHSADQ | (YK-1212), | (SEQ ID NO:5); |
| LYNEQFAVQGLLRYHTYARFQ | (YK-1215), | (SEQ ID NO:6); |
| HTYARFGIEIQVQINPTPFQ | (YK-1216), | (SEQ ID NO:7); |
| INPTPFQQGGLICAMVPGDQ | (YK-1217), | (SEQ ID NO:8); |
| HFKDPQYPVWELTIRVWSELQ | (YK-1222), | (SEQ ID NO:9); |
| NIGTGTSAYTSLNVLARFTDQ | (YK-1224), | (SEQ ID NO:10). |

In another embodiment, the synthetic peptide includes an amino acid sequence that is substantially similar to an antigenic portion of the VP3 protein of the HAV polyprotein and contains a Q amino acid residue at the C-terminal of the peptide. This synthetic peptide includes one or more of the amino acid sequences of SEQ ID NOS:11–22 and conservative variations thereof, or binds to an antibody specifically immunoreactive with one or more peptides having the amino acid sequences of SEQ ID NOS:11–22 and conservative variations thereof. These sequences, their laboratory designations, and the corresponding SEQ ID NOS are as follows:

| | | |
|---|---|---|
| SDPSQGGGIKITHFTTWTSIQ | (YK-1235), | (SEQ ID NO:11); |
| GGIKITHFTTWTSIPTLAAQ | (YK-1236), | (SEQ ID NO:12); |
| QFPFNASDSVGQQIKVIPVDQ | (YK-1241), | (SEQ ID NO:13); |
| FNASDSVGQQIKVIPVDPYFQ | (YK-1242), | (SEQ ID NO:14); |
| SDSVGQQIKVIPVDPYFFQMQ | (YK-1243), | (SEQ ID NO:15); |
| IKVIPVDPYFFQMTNTNPDQ | (YK-1244), | (SEQ ID NO:16); |
| KCITALASICQMFCFWRGDLQ | (YK-1247), | (SEQ ID NO:17); |
| FWRGDLVFDFQVFPTKYHSGQ | (YK-1248), | (SEQ ID NO:18); |
| FDFQVFPTKYHSGRLLFCFVQ | (YK-1249), | (SEQ ID NO:19); |
| FPTKYHSGRLLFCFVPGNELQ | (YK-1250), | (SEQ ID NO:20); |
| GITLKQATTAPCAVMDITGVQ | (YK-1252), | (SEQ ID NO:21); |
| VASHVRVNVYLSAINLECFAQ | (YK-1261), | (SEQ ID NO:22). |

In another embodiment, the synthetic peptide includes an amino acid sequence that is substantially similar to an antigenic portion of the VP1 protein of the HAV polyprotein and contains a Q amino acid residue at the C-terminal of the peptide. This synthetic peptide includes one or more of the amino acid sequences of SEQ ID NOS:23–38 and conservative variations thereof, or binds to an antibody specifically immunoreactive with one or more peptides having the amino acid sequences of SEQ ID NOS:23–38 and conservative variations thereof. These sequences, their laboratory designations, and the corresponding SEQ ID NOS are as follows:

| | |
|---|---|
| TTVSTEQNVPDPQVGITTMKQ (YK-1265), | (SEQ ID NO:23); |
| QNVPDPQVGITTMKDLKGKAQ (YK-1266), | (SEQ ID NO:24); |
| NRGKMDVSGVQAPVGAITTIQ (YK-1268), | (SEQ ID NO:25); |
| ITTIEDPVLAKKVPETFPELQ (YK-1271), | (SEQ ID NO:26); |
| EDPVLAKKVPETFPELKPGEQ (YK-1272), | (SEQ ID NO:27); |
| AKKVPETFPELKPGESRHTSQ (YK-1273), | (SEQ ID NO:28); |
| FPELKPGESRHTSDHMSIYKQ (YK-1274), | (SEQ ID NO:29); |
| DHMSIYKFMGRSHFLCTFTFQ (YK-1276), | (SEQ ID NO:30); |
| HFLCTFTFNSNNKEYTFPITQ (YK-1279), | (SEQ ID NO:31); |
| TPVGLAVDTPWVEKESALSIQ (YK-1290), | (SEQ ID NO:32); |
| LSFSCYLSVTEQSEFYFPRAQ (YK-1307), | (SEQ ID NO:33); |
| SVTEQSEFYFPRAPLNSNAMQ (YK-1308), | (SEQ ID NO:34); |
| PLNSNAMLSTESMMSRIAAGQ (YK-1310), | (SEQ ID NO:35); |
| MSRIAAGDLESSVDDPRSEEQ (YK-1312), | (SEQ ID NO:36); |
| AGDLESSVDDPRSEEDKRFEQ (YK-1313), | (SEQ ID NO:37); |
| VDDPRSEEDKRFESHIECRKQ (YK-1314), | (SEQ ID NO:38). |

In a further embodiment, the synthetic peptide includes an amino acid sequence that is substantially similar to an antigenic portion of the P2A protein of the HAV polyprotein and contains a Q amino acid residue at the C-terminal of the peptide. This synthetic peptide includes one or more of the amino acid sequences of SEQ ID NOS:39–48 and conservative variations thereof, or binds to an antibody specifically immunoreactive with one or more peptides having the amino acid sequences of SEQ ID NOS:39–48 and conservative variations thereof. These sequences, their laboratory designations, and the corresponding SEQ ID NOS are as follows:

SHIECRKPYKELRLEVGKQRQ (YK-1315), (SEQ ID NO:39);

PYKELRLEVGKQRLKYAQEEQ (YK-1316), (SEQ ID NO:40);

QRLKYAQEELSNEVLPPPRKQ (YK-1317), (SEQ ID NO:41);

VLPPPRKMKGLFSQAKISLFQ (YK-1318), (SEQ ID NO:42);

FSQAKISLFYTEEHEIMKFSQ (YK-1319), (SEQ ID NO:43);

KVNFPHGMLDLEEIAANSKDQ (YK-1327), (SEQ ID NO:44);

DLEEIAANSKDFPNMSETDLQ (YK-1328), (SEQ ID NO:45);

KINLADRMLGLSGVQEIKEQ (YK-1331), (SEQ ID NO:46);

QRLKYAQEELSNEVLPPPRKMKGLFQ (YK-1665), (SEQ ID NO:47);

WLNPKKINLADRMLGLSGVQEIKEQ (YK-1757), (SEQ ID NO:48).

In another embodiment, the synthetic peptide includes an amino acid sequence that is substantially similar to an antigenic portion of the P2B protein of the HAV polyprotein and contains a Q amino acid residue at the C-terminal of the peptide. This synthetic peptide includes the amino acid sequence of SEQ ID NOS:49 and conservative variations thereof, or binds to an antibody specifically immunoreactive with a peptide having the amino acid sequence of SEQ ID NO:49 and conservative variations thereof. The sequence, laboratory designations, and the corresponding SEQ ID NO is as follows:

VIQQLNQDEHSHIIGLLRVMQ (YK-1334), (SEQ ID NO:49).

In yet another embodiment, the synthetic peptide includes an amino acid sequence that is substantially similar to an antigenic portion of the P2C protein of the HAV polyprotein and contains a Q amino acid residue at the C-terminal of the peptide. This synthetic peptide includes one or more of the amino acid sequences of SEQ ID NOS:50–61 and conservative variations thereof, or binds to an antibody specifically immunoreactive with one or more peptides having the amino acid sequences of SEQ ID NOS:50–61 and conservative variations thereof. These sequences, their laboratory designations, and the corresponding SEQ ID NOS are as follows:

NILKDNQQKIEKAIEEADEFQ (YK-1341), (SEQ ID NO:50);

LGSINQAMVTRCEPVVCYLYQ (YK-1347), (SEQ ID NO:51);

RCEPVVCYLYGKRGGGKSLTQ (YK-1348), (SEQ ID NO:52);

TKPVASDYWDGYSGQLVCIIQ (YK-1352), (SEQ ID NO:53);

VSGCPMRLNMASLEEKGRHFQ (YK-1356), (SEQ ID NO:54);

LNMASLEEKGRHFSSPFIIAQ (YK-1357), (SEQ ID NO:55);

NPSPKTVYVKEAIDRRLHFKQ (YK-1360), (SEQ ID NO:56);

VKEAIDRRLHFKVEVKPASFQ (YK-1361), (SEQ ID NO:57);

VKPASFFKNPHNDMLNVNLAQ (YK-1362), (SEQ ID NO:58);

KNPHNDMLNVNLAKTNDAIKQ (YK-1363), (SEQ ID NO:59);

LAKTNDAIKDMSCVDLIMDGQ (YK-1364), (SEQ ID NO:60);

VMTVEIRKQNMTEFMELWSQ (YK-1367), (SEQ ID NO:61).

In a further embodiment, the synthetic peptide includes an amino acid sequence that is substantially similar to an antigenic portion of the P3A protein of the HAV polyprotein and contains a Q amino acid residue at the C-terminal of the peptide. This synthetic peptide includes one or more of the amino acid sequences of SEQ ID NOS:62–65 and conservative variations thereof, or binds to an antibody specifically immunoreactive with one or more peptides having the amino acid sequences of SEQ ID NOS:62–65 and conservative variations thereof. These sequences, their laboratory designations, and the corresponding SEQ ID NOS are as follows:

SQGISDDDNDSAVAEFFQSFQ (YK-1368), (SEQ ID NO:62);

DSAVAEFFQSFPSGEPSNSKQ (YK-1369), (SEQ ID NO:63);

FQSFPSGEPSNSKLSGFFQSQ (YK-1370), (SEQ ID NO:64);

SAVAEFFQSFPSGEPSNSKLSGFFQ (YK-1832), (SEQ ID NO:65).

In yet a further embodiment, the synthetic peptide includes an amino acid sequence substantially similar to an antigenic portion of the P3B protein of the HAV polyprotein and contains a Q amino acid residue at the C-terminal of the peptide. This synthetic peptide includes the amino acid sequence of SEQ ID NO:66 and conservative variations thereof, or binds to an antibody specifically immunoreactive with a peptide having the amino acid sequence of SEQ ID NO:66 and conservative variations thereof. The sequence, laboratory designations, and the corresponding SEQ ID NO is as follows:

HGVTKPKQVIKLDADPVESQ (YK-1374),    (SEQ ID NO:66).

In yet another embodiment, the synthetic peptide includes an amino acid sequence which is substantially similar to an antigenic portion of the P3C protein of the HAV polyprotein and contains a Q amino acid residue at the C-terminal of the peptide. This synthetic peptide includes one or more of the amino acid sequences of SEQ ID NOS:67–72 and conservative variations thereof, or binds to an antibody specifically immunoreactive with one or more peptides having the amino acid sequences of SEQ ID NOS:67–72 and conservative variations thereof. These sequences, their laboratory designations, and the corresponding SEQ ID NOS are as follows:

GLVRKNLVQFGVGEKNGCVRQ (YK-1376),    (SEQ ID NO:67);
DVVLMKVPTIPKFRDITQHFQ (YK-1382),    (SEQ ID NO:68);
MEEKATYVHKKNDGTTVDLTQ (YK-1388),    (SEQ ID NO:69);
KNDGTTVDLTVDQAWRGKGEQ (YK-1389),    (SEQ ID NO:70);
RGKGEGLPGMCGGALVSSNQ (YK-1390),    (SEQ ID NO:71);
VAKLVTQEMFQNIDKKIESQ (YK-1393),    (SEQ ID NO:72).

In yet another embodiment, the synthetic peptide includes an amino acid sequence which is substantially similar to an antigenic portion of the P3D protein of the HAV polyprotein and contains a Q amino acid residue at the C-terminal of the peptide. This synthetic peptide includes one or more of the amino acid sequences of SEQ ID NOS:73–88 and conservative variations thereof, or binds to an antibody specifically immunoreactive with one or more peptides having the amino acid sequences of SEQ ID NOS:73–88 and conservative variations thereof. These sequences, their laboratory designations, and the corresponding SEQ ID NOS are as follows:

RIMKVEFTQCSMNVVSKTLFQ (YK-1394),    (SEQ ID NO:73);
FTQCSMNVVSKTLFRKSPIYQ (YK-1395),    (SEQ ID NO:74);
MLSKYSLPIVEEPEDYKEASQ (YK-1399),    (SEQ ID NO:75);
LDENGLLLGVHPRLAQRILFQ (YK-1407),    (SEQ ID NO:76);
CPKDELRPLEKVLESKTRAIQ (YK-1411),    (SEQ ID NO:77);
SKTRAIDACPLDYSILCRMYQ (YK-1412),    (SEQ ID NO:78);
RMYWGPAISYFHLNPGFHTGQ (YK-1414),    (SEQ ID NO:79);
KTMIRFGDVGLDLDFSAFDAQ (YK-1418),    (SEQ ID NO:80);
DLDFSAFDASLSPFMIREAGQ (YK-1419),    (SEQ ID NO:81);
INNVNLYYVFSKIFGKSPVFQ (YK-1424),    (SEQ ID NO:82);
GQKIVDEFKKLGMTATSADKQ (YK-1428),    (SEQ ID NO:83);
LGMTATSADKNVPQLKPVSEQ (YK-1429),    (SEQ ID NO:84);
PQLKPVSELTFLKRSFNLVEQ (YK-1431),    (SEQ ID NO:85);
SEKTIWSLIAWQRSNAEFEQ (YK-1434),    (SEQ ID NO:86);
SLIAWQRSNAEFEQNLENAQ (YK-1435),    (SEQ ID NO:87);
WQRSNAEFEQNLENAQWFAFQ (YK-1436),    (SEQ ID NO:88).

More preferably, the synthetic peptide includes one or more of the amino acid sequences of SEQ ID NOS:41 (YK-1317), 47 (YK-1665), 62 (YK-1368), 63 (YK-1369), 66 (YK-1374) and 72 (YK-1393), and conservative variations thereof, or binds to an antibody specifically immunoreactive with one or more peptides having the amino acid sequences of SEQ ID NOS:41, 47, 62, 63, 66, 72, and conservative variations thereof.

Most preferably, the synthetic peptide includes the amino acid sequence of SEQ ID NO:47 or binds to an antibody specifically immunoreactive with a peptide having the amino acid sequence of SEQ ID NO:47.

In a principal embodiment of the present invention a method of detecting the presence of antibodies specific for HAV in a biological fluid is provided, said method including contacting one or more of the synthetic peptides described herein with the biological fluid and detecting the formation of complexes between the immunogenic peptide and antibodies present in the biological fluid. Detection assays suitable for the present invention include those known to those skilled in the art.

In a further embodiment, the present invention provides a method of differentiating between vaccine-induced immunity and natural HAV immunity. This method comprises contacting an isolated, nonstructural, immunogenic HAV peptide of the present invention with antibodies from mammalian serum. The formation of complexes between the immunogenic peptide and the antibodies are then detected, wherein the presence of peptide-antibody complexes indicates natural HAV immunity. Examples of suitable nonstructural immunogenic peptides suitable for use in this method of the present invention include, but are not limited to, peptides comprising an amino acid sequence of SEQ ID NOS:39–72.

In another aspect, the present invention provides an immunogenic composition comprising a pharmaceutically acceptable carrier and one or more of the synthetic peptides described above in an amount sufficient to induce an immune response to HAV in a mammal. Preferably, the immune response confers a protective effect or prevents subsequent HAV infection in an animal to which the composition has been administered. In a preferred embodiment, the immunogenic peptide is covalently attached (conjugated) to a carrier protein. Suitable carriers include, but are not limited to, serum albumin, keyhole limpet hemocyanin, diphtheria toxin, tetanus toxin and synthetic polymers such as poly(D-Leu:D-Glu). As such, the present invention also provides immunogenic conjugates, such conjugates containing a carrier protein covalently attached to one or more of the synthetic peptides described herein.

In a further aspect, the present invention provides a method of inducing an immune response to HAV in a mammal, the method comprises administering to the mammal an immunologically effective amount of a pharmaceutical composition comprising a pharmaceutically acceptable carrier and one or more of the synthetic peptides described herein.

In another embodiment, the present invention provides a method of making an antibody that is specific for HAV. The method includes administering one or more of the synthetic peptides described herein to an animal, collecting blood from the animal, and isolating anti-HAV specific antibodies from the blood in accordance with methods known to those skilled in the art. It will be understood that the antibodies include both polyclonal and monoclonal antibodies. Methods for the production of both polyclonal and monoclonal antibodies are well known in the art.

In another aspect, the present invention provides isolated DNA sequences encoding one or more of the synthetic peptides described herein.

In a further aspect, diagnostic kits are provided. In one embodiment, a kit for the diagnosis of HAV includes a container and one or more of the synthetic peptides described herein. Preferably, the kit further contains instructional materials and reagents for carrying out a diagnostic test for HAV. In another embodiment, a kit for differentiating between vaccine-induced immunity and natural HAV immunity is provided. The kit includes a container and one or more synthetic peptides containing antigenic epitopes from the nonstructural region of the HAV polypeptide. Preferably, the kit also contains instruction materials and reagents for carrying out the differentiation test.

Peptide Synthesis

The synthetic peptides described herein generally contain from about 9 to about 35 amino acid residues, more preferably, from about 15 to about 30 amino acid residues and, even more preferably, from about 20 to about 25 amino acid residues. Because the peptides are relatively short in length, they can be prepared using any of a number of chemical peptide synthesis techniques well known to those of ordinary skill in the art including solution methods and solid phase methods, with solid phase synthesis being presently preferred.

In particular, solid phase synthesis in which the C-terminal amino acid of the peptide sequence is attached to an insoluble support followed by sequential addition of the remaining amino acids in the sequence is the preferred method for preparing the peptides. Techniques for solid phase synthesis are described by Barany and Merrifield, *Solid-Phase Peptide Synthesis*, in *The Peptides: Analysis, Synthesis, Biology* (Gross and Meienhofer (eds.), Academic Press, N.Y., vol. 2, pp. 3–284 (1980)); Merrifield et al., *J. Am. Chem. Soc.* 85, 2149–2156 (1963); and Stewart et al., *Solid Phase Peptide Synthesis* (2nd ed., Pierce Chem. Co., Rockford, Ill. (1984)). Many automated systems for performing solid phase peptide synthesis are commercially available.

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those skilled in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins, and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenz-hydrylamine resin as the solid support. Those skilled in the art will recognize that when the BHA or MBHA resin is used, treatment with anhydrous hydrofluoric acid to cleave the peptide from the solid support produces a peptide having a terminal amide group.

The α-amino group of each amino acid used in the synthesis should be protected during the coupling reaction to prevent side reactions involving the reactive α-amino function. Certain amino acids also contain reactive side-chain functional groups (e.g., sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, *The Peptides: Analysis, Synthesis, Biology, Vol. 3: Protection of Functional Groups in Peptide Synthesis* (Gross and Meienhofer (eds.), Academic Press, N.Y. (1981)).

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the α-amino protecting group, and must be removable after completion of the peptide synthesis under conditions that will not alter the structure of the peptide.

Illustrative examples of protecting groups for an α-amino group include, but are not limited to, the following: aromatic urethane-type groups such as, for example, fluorenylmethyloxycarbonyl (Fmoc), carbobenzoxy (Cbz), and substituted benzyloxycarbonyls, including p-chlorobenzyloxycarbonyl, o-chlorobenzyloxycarbonyl, 2,4-dichlorobenzyloxycarbonyl, 2,6-dichlorobenzyloxycarbonyl, etc.; aliphatic urethane-type groups such as, for example, butyloxycarbonyl (Boc), t-amyloxycarbonyl, isopropyloxycarbonyl, 2-(p-biphenylyl)-isopropyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the α-amino protecting group used.

For the side chain amino group present in lysine (Lys), any of the protecting groups described above for the protection of the α-amino group are suitable. Moreover, other suitable protecting groups include, but are not limited to, the following: butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyl-oxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethyl-benzenesulfonyl and 2,2,5,7,8-pentamethylchloroman-6-sulfonyl are the protecting group used for Arg.

The hydroxyl group on the side chains of serine (Ser), threonine (Thr) or tyrosine (Tyr) can be protected by a $C_1$-$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxylprotecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group.

The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of techniques known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology, Vol. 1: Methods of peptide Bond Formation* (Gross and Meienhofer (eds.), Academic Press, N.Y. (1979)); and Izumiya, et al., *Synthesis of Peptides* (Maruzen Publishing Co., Ltd., (1975)).

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl) phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Novartis (Switzerland) or Bachem (California)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art. It should be noted that because the immunogenic HAV peptides of the present invention are relative short in length, this latter approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2CL_2$), or mixtures thereof. If coupling is incomplete, the coupling reaction may be repeated before deprotection of the N-amino group and addition of the next amino acid. Coupling efficiency may be monitored by a number of means well known to those of skill in the art. A preferred method of monitoring coupling efficiency is by the ninhydrin reaction. Peptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably about 60 minutes; by bubbling hydrogen bromide (HBr) continuously through a 1 mg/10 mL suspension of the resin in trifluoroacetic acid (TFA) for about 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skill in the art. For example, the peptides may be purified using known chromatographic procedures such as reverse phase HPLC, gel permeation, ion exchange, size exclusion, affinity, partition, or countercurrent distribution.

Although the synthetic peptides are preferably prepared or produced using chemical peptide synthesis techniques such as described above, it will be understood by those of ordinary skill in the art that they can also be prepared by other means including, for example, recombinant techniques. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA Chemical Company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

The nucleic acid compositions of this invention, whether RNA, or DNA are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences for generating nucleic acid fragments for subsequent subcloning are known. Examples of techniques sufficient to direct persons of skill through such in vitro amplification methods, including the polymerase chain reaction (PCR), the ligase chain reaction (LCR), Qb-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35,1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13:563–564. Improved methods of cloning in vitro amplified nucleic acids are described in Wallace et al., U.S. Pat. No. 5,426,039.

Small nucleic acids (less than 100 nucleotides in length) are typically synthesized chemically according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Nucleic acids can also be custom made and ordered from a variety of commercial sources known to persons of skill. Purification, where necessary, is typically performed by either native acrylamide gel electrophoresis or by anion-exchange HPLC as described in Pearson and Regnier (1983) *J. Chrom.* 255:137–149. The sequence of synthetic oligonucleotides can be verified using the chemical degradation method of Maxam and Gilbert (1980) in Grossman and Moldave (eds.) Academic Press, New York, *Methods in Enzymology* 65:499–560.

Nucleic Acids Encoding Immunogenic HAV Peptides

The entire HAV genomic sequence has been deposited with GeneBank and access to the HAV nucleic acid sequence can be obtained from GeneBank by reference to the following accession numbers: X75214; X83302; K02990; M14707; M59808; M59810; M59809; and M16632. The sequences are incorporated by reference herein.

Therefore, nucleic acid molecules encoding the immunogenic HAV peptide sequences disclosed herein are also provided. One of skill in the art will recognize a variety of equivalent nucleic acids which encode the peptides described herein. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid arginine. Thus, at every position where an arginine is to be encoded by a nucleic acid triplet, the nucleic acid has any of the triplets which encode arginine. One of skill is thoroughly familiar with the genetic code and its use. An introduction to the subject is found in, for example, chapter 15 of Watson, et al., *Molecular Biology of the Gene* (Fourth Edition, The Benjamin/Cummings Company, Inc., Menlo Park, Calif. (1987)), and the references cited therein.

Although any nucleic acid triplet or codon which encodes an amino acid can be used to specify the position of the amino acid in a peptide, certain codons are preferred. It is desirable to select codons for elevated expression of an encoded peptide, for example, when the peptide is purified for use as an immunogenic reagent. Codons are selected by reference to species codon bias tables, which show which codons are most typically used by the organism in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated. Codon bias tables are available for most organisms. For an introduction to codon bias tables, see, e.g., Watson et al., supra.

Conservative Substitutions

In addition, it will be readily apparent to those of ordinary skill in the art that the synthetic peptides described herein and the nucleic acid molecules encoding such immunogenic peptides can be subject to various changes, such as insertions, deletions, and substitutions, either conservative or non-conservative, where such changes might provide for certain advantages in their use, i.e., to increase biological activity.

One skilled in the art will appreciate that many conservative variations of nucleic acid constructs yield a functionally identical construct. For example, due to the degeneracy of the genetic code, silent substitutions (i.e., substitutions of a nucleic acid sequence which do not result in an alteration in an encoded peptide) are an implied feature of every nucleic acid sequence which encodes an amino acid. In addition, one skilled in the art will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Ausbel, Berger and Kimmel, all supra.

Modifications to nucleic acids are evaluated by routine screening techniques in suitable assays for the desired characteristic. For instance, changes in the immunological character of encoded peptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Similarly, conservative amino acid substitutions, wherein one or a few amino acids in an amino acid sequence of a protein are substituted having different amino acids with highly similar properties (see, the definitions section, supra), are also readily identified as being highly similar to a disclosed construct. By conservative substitutions is meant replacing an amino acid residue with another which is biologically and/or chemically similar, e.g., one hydrophobic residue for another, or one polar residue for another. These substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are a feature of the present invention.

Mosaic Proteins

In an alternative embodiment, the synthetic peptides described herein are combined into mosaic proteins. Typically, 2 to 20 of the peptides are fused into a single polypeptide by recombinant or synthetic techniques.

In recombinant procedures, mosaic proteins are made by ligating synthetic or recombinant nucleic acids which encode immunogenic peptides. These nucleic acids are ligated enzymatically (e.g., using a DNA ligase enzyme) or synthetically. Alternatively, a single nucleic acid is synthesized which encodes multiple immunogenic peptides. In either case, the resulting nucleic acid encodes multiple immunogenic peptides, all in the same reading frame. Thus, the translated polypeptide comprises immunogenic peptide domains.

When the mosaic proteins are made by automated chemical synthetic procedures, concatamers of peptides are coupled directly. This coupling is performed chemically by joining peptides using standard chemical methods. Alternatively, a polynucleotide is synthetically produced that encodes multiple immunogenic peptides.

Chemical or recombinant linker regions are optionally included between immunogenic peptide domains to facilitate presentation of the domains to antibodies which bind the domains. In preferred embodiments, 10–50 amino acids are inserted between immunogenic domains. Essentially any amino acid, or chemical moiety which forms amide and carboxyl linkages can be used as a linker.

Diagnostic and Screening Assays

The synthetic HAV peptides, antibodies and nucleic acids of the invention are useful in a number of different diagnostic applications. For instance, labeled polypeptides of the invention can be used to detect the presence of antibodies to HAV in a biological sample. Alternatively, labeled antibodies, particularly monoclonal antibodies, to polypeptides of the invention can be used to detect HAV in a biological sample.

More particularly, in one embodiment, the present invention provides a method of detecting the presence of antibodies against HAV in mammalian serum, the method involving contacting an isolated, immunogenic HAV peptide of the present invention with antibodies from mammalian serum, and detecting the formation of complexes between the immunogenic peptide and the antibodies. In a preferred embodiment, a number of different immunogenic HAV peptides are used. A particularly preferred combination of immunogenic HAV polypeptides comprises one or more peptides having the following amino acid sequence:

| | |
|---|---|
| QRLKYAQEELSNEVLPPPRKMKGLFQ (YK-1665), | (SEQ ID NO:47); |
| WLNPKKINLADRMLGLSGVQEIKEQ (YK-1757), | (SEQ ID NO:48); |
| SAVAEFFQSFPSGEPSNSKLSGFFQ (YK-1832), | (SEQ ID NO:65); | and conservative variations thereof.

In another embodiment, the present invention provides a method of differentiating between vaccine-induced immunity and natural HAV immunity, the method involving contacting an isolated, nonstructural, immunogenic HAV peptide of the present invention with antibodies from mammalian serum, and detecting the formation of complexes between the immunogenic peptide and the antibodies, wherein the presence of peptide-antibody complexes indicates natural HAV immunity. In a preferred embodiment, a number of different nonstructural HAV immunogenic peptides are used in this method. A particularly preferred combination of immunogenic HAV polypeptides includes one or more peptides having the following amino acid sequence:

| | |
|---|---|
| QRLKYAQEELSNEVLPPPRKMKGLFQ (YK-1665), | (SEQ ID NO:47); |
| WLNPKKINLADRMLGLSGVQEIKEQ (YK-1757), | (SEQ ID NO:48); |
| SAVAEFFQSFPSGEPSNSKLSGFFQ (YK-1832), | (SEQ ID NO:65); | and conservative variations thereof.

In yet another embodiment, the present invention provides a method of detecting acute phase infection. The method involves contacting an isolated, immunogenic HAV peptide of the present invention with antibodies from mammalian serum and detecting the IgM antibodies that bind to the immunogenic peptides of the present invention. The detection of IgM antibodies can be performed with a labeled secondary antibody that recognizes IgM antibodies. In a preferred embodiment, a number of different immunogenic HAV peptides are used in this method.

In a further embodiment, the present invention provides a method of detecting convalescence in a mammal. This method involves contacting an isolated, immunogenic HAV peptide of the present invention with antibodies from mammalian serum and detecting total antibody titer by measuring binding to the immunogenic peptides of the present invention. Such antibodies include, but are not limited to, IgG, IgM, IgE, and the like.

Immunogenic Conjugates

Immunogenic conjugates containing one or more of the synthetic HAV peptides described above, covalently attached to a carrier protein, are also provided. Suitable carrier proteins include, but are not limited to, the following: thyroglobulin; albumins, such as human serum albumin; tetanus toxoid; polyamino acids, such as poly(D-lysine: D-glutamic acid); influenza; hepatitis B virus core protein; hepatitis B virus recombinant vaccine; and the like.

When the peptide and carrier protein are relatively short in length (i.e., less than about 50 amino acids), they are preferably synthesized using standard chemical peptide synthesis techniques. When both molecules are relatively short, a chimeric molecule is optionally synthesized as a single contiguous polypeptide. Alternatively, the peptide and the carrier molecule can be synthesized separately and then fused chemically.

Solid phase synthesis in which the C-terminal amino acid of the sequence is attached to an insoluble support followed by sequential addition of the remaining amino acids in the sequence is a preferred method for the chemical synthesis of the immunogenic conjugates provided herein. Techniques for solid phase synthesis are described by Barany and Merrifield, *Solid-Phase Peptide Synthesis*; pp. 3–284 in *The*

*Peptides: Analysis, Synthesis, Biology. Vol. 2: Special Methods in Peptide Synthesis, Part A.*; Merrifield et al. *J. Am. Chem. Soc.*, 85:2149-2156 (1963); and Stewart et al., *Solid Phase Peptide Synthesis*, 2$^{nd}$ ed. Pierce Chem. Co., Rockford, Ill. (1984).

Alternatively, the immunogenic conjugates are synthesized using recombinant nucleic acid methodology. Generally, this involves creating a nucleic acid sequence that encodes the peptide-carrier protein immunogenic conjugate, placing the nucleic acid in an expression cassette under the control of a particular promoter, expressing the protein in a host, isolating the expressed protein and, if required, renaturing the protein. Techniques sufficient to guide one of skill through such procedures are found in, e.g., Berger and Kimmel, Sambrook, and Ausubel at the citations provided above.

While the peptide and carrier molecule are often joined directly together, one of skill will appreciate that the molecules may be separated by a spacer molecule (e.g., a peptide) consisting of one or more amino acids. Generally, the spacer will have no specific biological activity other than to join the immunogenic peptide to the carrier protein, or to preserve some minimum distance or other spatial relationship between them. However, the constituent amino acids of the spacer may be selected to influence some property of the molecule such as the folding, net charge, or hydrophobicity.

Once expressed, recombinant immunogenic conjugates can be purified according to standard procedures, including ammonium sulfate precipitation, affinity columns, column chromatography, gel electrophoresis and the like (see, generally, R. Scopes, *Protein Purification*, Springer-Verlag, N.Y. (1982) and Deutscher, *Methods in Enzymology Vol. 182: Guide to Protein Purification*, Academic Press, Inc. N.Y. (1990)). Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the immunogenic conjugates of the present invention may possess a conformation substantially different than the native conformations of the constituent peptides. In this case, it is often necessary to denature and reduce the polypeptide and then to cause the polypeptide to re-fold into the preferred conformation. Methods of reducing and denaturing proteins and inducing re-folding are well known to those of skill in the art.

Antibody Production and Immunoassays

The present invention also provides antibodies that can be raised to the synthetic peptides described above, including individual, allelic, strain, or species variants, and fragments thereof, both in their naturally occurring (full-length) forms and in recombinant forms. Additionally, the antibodies can be raised to these peptides in either their native configurations or in non-native configurations. Anti-idiotypic antibodies can also be generated. Many methods of making antibodies are known to persons of skill.

A particular peptide, protein, or antibody can be quantified by a variety of immunoassay methods. For a review of immunological and immunoassay procedures in general, see Stites and Terr (eds.), *Basic and Clinical Immunology* (7th ed.) (1991). Moreover, the immunoassays can be performed in any of several configurations, e.g., those reviewed in Maggio (ed.) *Enzyme Immunoassay* CRC Press, Boca Raton, Fla. (1980); Tijan, "*Practice and Theory of Enzyme Immunoassays,*" *Laboratory Techniques in Biochemistry and Molecular Biology*, Elsevier Science Publishers B. V., Amsterdam (1985); Harlow and Lane, supra; Chan (ed.) *Immunoassay: A Practical Guide* Academic Press, Orlando, Fla. (1987); Price and Newman (eds.) *Principles and Practice of Immunoassays* Stockton Press, NY (1991); and Ngo (ed.) *Non isotopic Immunoassays* Plenum Press, NY (1988).

Immunoassays often utilize a labeling agent to specifically bind and label the binding complex formed by the capture agent and the analyte. The labeling agent may itself be one of the moieties comprising the peptide/antibody complex. Thus, the labeling agent may be a labeled peptide or a labeled anti-peptide antibody. Alternatively, the labeling agent may be a third moiety, such as another antibody, that specifically binds to the antibody/peptide complex, or to a modified capture group (e.g., biotin) which is covalently linked to the peptide or anti-peptide antibody.

Immunoassays for detecting a peptide or an antibody to a peptide may be either competitive or noncompetitive. Noncompetitive immunoassays are assays in which the amount of captured analyte (e.g., anti-peptide antibody) is directly measured. In competitive assays, the amount of analyte (e.g., immunogenic peptide or antibody to an immunogenic peptide) present in the sample is measured indirectly by measuring the amount of an added (exogenous) analyte displaced (or competed away) from a capture agent (e.g., an antibody or peptide) by the analyte present in the sample.

Sample Collection and Processing

One or more of the synthetic peptides described herein, or alternatively, one or more of the antibodies to the synthetic peptides are preferably quantified in a biological sample, such as a biological fluid or tissue sample derived from a patient. The detection of HAV peptides or HAV antibodies indicates that the human or animal from whom the biological sample was taken is infected with HAV. A determination of the quantity of antibodies or protein present in the biological sample may be indicative of the severity of the disease or the response to treatment.

The sample to be tested or analyzed may be obtained from any biological source and is preferably taken from a human or animal capable of being infected with or harboring HAV. For example, the sample may be a cell sample, tissue sample or biological fluid, such as whole blood, blood serum, blood plasma, urine, semen, saliva, sputum, cerebrospinal fluid, lacrimal fluid, fermentation fluid, lymph fluid, tissue culture fluid, ascites fluid, synovial fluid, pleural fluid, and the like. The preferred biological sample is a biological fluid from which cells can be removed. The most preferred samples are blood plasma or serum. The biological sample may also be a laboratory research sample such as a cell culture supernatant, viral isolate or viral concentrate. The sample is collected or obtained using methods well known to those skilled in the art.

Although the sample is typically taken from a human patient, the assay can be used to detect antibodies or HAV peptides or proteins in samples taken from eukaryotes in general and, in particular, mammals, such as dogs; cats; sheep; cattle; pigs; primates, such as chimpanzees, gorillas, macaques, and baboons; and rodents, such as mice, rats, and guinea pigs.

The sample may be diluted, purified, concentrated, filtered, dissolved, suspended or otherwise manipulated prior to use in the assay. Preferably, a sample containing particulate matter is diluted, filtered, or both diluted and filtered prior to use. The preferred diluent is a buffer solution. Any of a number of standard aqueous buffer solutions, employing one of a variety of buffers, such as phosphate, TRIS™ detergent, or the like, at physiological pH can be used.

The sample size for the biological fluid sample is preferably between approximately 0.5 µl and 1 ml. A preferred biological fluid sample size is between approximately 1 and 100 µl. More preferably, the volume of the biological fluid sample is approximately 10 to 50 µl.

Quantification

An immunogenic peptide or, alternatively, an antibody to HAV can be detected and quantified by any of a number of means well known to those skilled in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those skilled in the art. Typically, this involves coating the substrate with a proteinaceous composition. In particular, protein compositions such as bovine serum albumin (BSA), nonfat powdered milk, and gelatin are widely used.

Other Assay Formats

Western blot analysis can also be used to detect and quantify the presence of an immunogenic peptide in the sample. The technique generally comprises separating sample products by gel electrophoresis on the basis of molecular weight, transferring the separated proteins to a suitable solid support (such as a nitrocellulose filter, a nylon filter, or derivatized nylon filter), and incubating the sample with the antibodies that specifically bind immunogenic HAV peptides. The anti-peptide antibodies specifically bind to a peptide fixed on the solid support.

These antibodies are directly labeled or, alternatively, they may be subsequently detected using labeled antibodies (e.g., labeled sheep anti-mouse antibodies where the antibody to a peptide is a murine antibody) that specifically bind to the anti-peptide antibody.

Other assay formats include liposome immunoassays (LIAs), which use liposomes designed to bind specific molecules (e.g., antibodies) and release encapsulated reagents or markers. The released chemicals are then detected according to standard techniques.

Labels

The labeling agent used to label the synthetic peptide or antibody can be, e.g., a peptide, a monoclonal antibody, a polyclonal antibody, an immunogenic peptide or a mosaic polypeptide of immunogenic peptides, or complex such as those described herein, or a polymer such as an affinity matrix, carbohydrate or lipid. Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include, but are not limited to, magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, and $^{32}$P), enzymes (e.g., LacZ, CAT, horse radish peroxidase, alkaline phosphatase and others, commonly used as detectable enzymes, either in an EIA or in an ELISA), and colorimetric labels such as colloidal gold or colored glass or plastic (e.g., polystyrene, polypropylene, latex, etc.) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDS) or photomultipliers and the like. Similarly, enzymatic labels are detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Substrates

As mentioned above, depending upon the assay, various components, including the immunogenic HAV peptide, anti-peptide antibody, or anti-idiotypic antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glass, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Pooled Antisera

A peptide that specifically binds to or is specifically immunoreactive with an antibody generated against a defined immunogen, such as an immunogenic HAV peptide comprising of the amino acid sequences described herein can be determined using the immunoassays described herein. In one embodiment, the immunoassay uses a polyclonal antiserum which is raised to the immunogenic peptide. This antiserum is selected to have low crossreactivity against known peptides, and any such reactivity is removed by immunoabsorbtion prior to use in the immunoassay.

In order to produce antisera for use in an immunoassay, the synthetic immunogenic peptides of the invention are made and isolated as described herein. For example, recombinant protein can be produced in a mammalian or other eukaryotic cell line, or the peptides can be made synthetically. An inbred strain of mice is immunized with a selected peptide using a standard adjuvant, such as Freund's adjuvant, and a standard mouse immunization protocol (see, Harlow and Lane, supra). Alternatively, a synthetic peptide derived from the sequences disclosed herein and conjugated to a carrier protein is used as an immunogen as described above in the section relating to immunogenic conjugates.

Polyclonal sera are collected and titered against the immunogenic peptide in an immunoassay, for example, a solid phase immunoassay with the immunogen immobilized on a solid support. Polyclonal antisera with a titer of $10^4$ or greater are selected and tested for their cross reactivity against any known protein, using a competitive binding immunoassay, such as the one described in Harlow and Lane, supra, at pages 570–573.

Immunoassays in the competitive binding format are used for crossreactivity determinations. For example, the immunogenic peptide is immobilized to a solid support. Proteins added to the assay compete with the binding of the antisera to the immobilized antigen. The ability of the above proteins to compete with the binding of the antisera to the immobilized protein is compared to the immunogenic peptide. The percent crossreactivity for the above proteins is calculated, using standard calculations. Those antisera with less than 10% crossreactivity with selected competitor proteins are selected and pooled. The cross-reacting antibodies are then removed from the pooled antisera by immunoabsorbtion with the competitor proteins.

The immunoabsorbed and pooled antisera are then used in a competitive binding immunoassay to compare the binding of a test peptide to the immunogenic peptide. In order to make this comparison, the two peptides are each assayed at a wide range of concentrations and the amount of each peptide required to inhibit 50% of the binding of the antisera to the immobilized protein is determined using standard techniques. If the amount of the test peptide required is less than twice the amount of the immunogenic peptide that is required, then the test peptide is said to specifically bind to an antibody generated to the immunogenic peptide.

As a final determination of specificity, the pooled antisera is fully immunosorbed with the immunogenic peptide against which the antisera was generated until no binding to the immunogenic peptide used in the immunosorbtion is detectable. The fully immunosorbed antisera is then tested for reactivity with the test peptide. If no reactivity is observed, then the test peptide is specifically bound by the antisera elicited by the immunogenic protein.

For further information concerning antibody production and immunoassay, see the published PCT application by Fields et al., WO 97/40147.

Pharmaceutical Compositions

The immunogenic HAV peptides described herein are useful in therapeutic and prophylactic applications for the treatment of HAV. For instance, in one embodiment, a method of inducing an immune response to HAV in a mammal is provided. The method involves administering to the mammal an immunologically effective amount of a pharmaceutical composition comprising a pharmaceutically acceptable carrier and one or more of the isolated, immunogenic HAV peptides described herein. In addition, a method of making an antibody against HAV is provided. This method involves administering an immunogenic HAV peptide of the present invention to a mammal.

Immunogenic or pharmaceutical compositions are described in which the compositions generally contain an immunogenic HAV peptide as described herein and a pharmaceutically acceptable carrier. Such compositions are suitable for use in a variety of drug delivery systems. Suitable formulations for use in the present invention are found in *Remington's Pharmaceutical Sciences*, Mack Publishing Company, Philadelphia, Pa., 17$^{th}$ ed. (1985). For a brief review of methods for drug delivery, see, Langer, *Science* 249:1527–1533 (1990).

The immunogenic HAV peptides described herein can be used in pharmaceutical and vaccine compositions that are useful for administration to mammals, particularly humans. The immunogenic peptides can be administered together in different combinations. The compositions are suitable for single administrations or a series of administrations. When given as a series, inoculations subsequent to the initial administration are given to boost the immune response and are typically referred to as booster inoculations.

The pharmaceutical compositions provided herein are intended for parenteral, topical, oral or local administration. Preferably, the pharmaceutical compositions are administered parenterally, e.g., intravenously, subcutaneously, intradermally, or intramuscularly. Thus, compositions are provided for parenteral administration that include a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%-75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount administered to the patient will vary depending upon what is being administered, the state of the patient and the manner of administration. In therapeutic applications, compositions are administered to a patient already suffering from HAV in an amount sufficient to inhibit spread of the virus, or at least partially arrest the symptoms of the disease and its complications. An amount adequate to accomplish this is defined as "therapeutically effective dose." Amounts effective for this use will depend on the severity of the disease, the particular composition, and the weight and general state of the patient. Generally, the dose will be in the range of about 1 mg per kg to about 5 mg per kg per day, preferably a total of about 100 mg per day, for a 70 kg patient.

Alternatively, the immunogenic HAV peptides are used prophylactically as vaccines. All of the immunogenic peptides disclosed herein can be used as vaccines. The vaccines of the invention contain as an active ingredient an immunogenically effective amount of the immunogenic HAV peptide or a combination of immunogenic HAV peptides. The immune response may include the generation of antibodies, activation of cytotoxic T lymphocytes (CTL) against cells presenting the immunogenic HAV peptides, or other mechanisms well known in the art.

In a preferred embodiment, the immunogenic HAV peptides are covalently attached (conjugated) to a carrier protein as described above. Useful carrier proteins include, but are not limited to, thyroglobulin; albumins, such as human serum albumin; tetanus toxoid; polyamino acids, such as poly(D-lysine:D-glutamic acid); influenza; hepatitis B virus core protein; and hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

In addition, DNA or RNA encoding the immunogenic HAV peptides of the present invention may be introduced into patients to obtain an immune response to the immunogenic peptides which the nucleic acid encodes. See, Wolff et al., *Science* 247:1465–1468 (1990), which describes the use of nucleic acids to produce expression of the immunogenic HAV peptides which the nucleic acids encode.

Vaccine compositions containing the immunogenic HAV peptides and nucleic acids of the invention are administered to a patient to elicit a protective immune response against the polypeptide. A "protective immune response" is one which prevents or inhibits the spread of HAV and, thus, at least partially prevents the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 mg to about 1 gm of peptide for a 70 kg patient, followed by boosting dosages of from about 100 mg to about 1 gm of the peptide pursuant to a boosting regimen over weeks to months depending upon the patient's response and condition, e.g., by measuring levels of HAV in the patient's blood. For nucleic acids, typically 30–1000 mg of nucleic acid is injected into a 70 kg patient, more typically about 150–300 mg of nucleic acid is injected into a 70 kg patient followed by boosting doses as appropriate.

The invention will be described in greater detail by way of specific examples. The following examples are offered for illustrative purposes, and are intended neither to limit or define the invention in any manner.

EXAMPLES

Example 1

Immunoreactivity of Synthetic HAV Peptides

Artificially designed synthetic peptides were tested for immunoreactivity to determine the effect of the presence of a Q residue at the C-terminal end of the peptide.

Peptides were synthesized by FMOC chemistry on an ACT Model MPS 350 multiple peptide synthesizer (Advanced Chemtech, Louisville, Ky.) according to the manufacturer's protocols. After characterization by amino acid analysis, high performance liquid chromatography, and capillary electrophoresis, peptides were characterized by enzyme immunoassay. For further discussion of methods and protocols used, see Chang J. C. et al., *Virology* 257: 177–190 (1999).

The synthetic peptides contained the sequences set forth in Table 1 below.

TABLE 1

Synthetic peptide sequences

| Peptide | Sequence | SEQ ID NO. |
|---|---|---|
| A | AAAAAAAAAAAAAAAAAAAAA | SEQ ID NO:89 |
| AQ | AAAAAAAAAAAAAAAAAAAAQ | SEQ ID NO:90 |
| G | GGGGGGGGGGGGGGGGGGGGG | SEQ ID NO:91 |
| GQ | GGGGGGGGGGGGGGGGGGGGQ | SEQ ID NO:92 |
| GA | GGGGGAAAAAGGGGGAAAAA | SEQ ID NO:93 |
| GAQ | GGGGGAAAAAGGGGGAAAAAQ | SEQ ID NO:94 |

The synthetic peptides were tested against a small panel of serum specimens composed of 32 anti-HAV IgM-positive sera and 40 anti-HAV negative sera. The peptides AQ, GQ, and GAQ showed specific immunoreactivity with anti-HAV IgM antibodies. Peptide GAQ demonstrated the broadest immunoreactivity. Peptide GAQ immunoreacted with IgM antibodies from 75% of anti-HAV positive sera and failed to show any immunoreactivity with negative control sera. Peptides A, G, and GA demonstrated negative reactivity. Therefore, the synthetic peptides having an artificially designed primary structure that was not identical to HAV, modeled HAV-specific IgM-reactive antigenic epitopes when the amino acid Q was added to the C-terminus.

A peptide having the sequence QRLKYAQEELSNEVLP-PPRKMKGLFQ (SEQ ID NO:47) was synthesized as described above and tested with a panel of anti-HAV positive sera obtained from acutely HAV-infected patients. This peptide was shown to react with up to 97% of anti-HAV IgM positive sera. Some serum specimens, which were not reactive with a peptide having the same sequence except without the Q residue at the C-terminus, or were not reactive with peptide GAQ, demonstrated reactivity with this synthetic peptide (SEQ ID NO:47).

The disclosures of all publications and patents cited in this application are hereby incorporated by reference in their entireties in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method for detecting the presence of antibodies against Hepatitis A virus in a subject, comprising contacting antibodies from the subject with one or more synthetic peptides that are immunoreactive with antibodies directed against Hepatitis A virus (HAV), wherein the peptide is at least nine amino acid residues in length to 35 amino acid residues in length with one molecules of the amino acid glutamine at the carboxyl terminal, and detecting binding of the peptides to the antibodies, wherein detecting binding of the peptides to the antibodies indicates the presence of antibodies against Hepatitis A virus in the subject.

2. The method of claim 1, wherein the antibodies are in a biological sample from the subject.

3. A method for detecting acute phase infection of Hepatitis A virus in a subject, comprising contacting antibodies from the subject with one or more synthetic peptides that are immunoreactive with antibodies directed against Hepatitis A virus (HAV), wherein the peptide is at least nine amino acid residues in length to 35 amino acid residues in length with one molecules of the amino acid glutamine at the carboxyl terminal, and detecting binding of the peptide to Igm antibodies against Hepatitis A virus, wherein detecting binding of the peptide to Igm antibodies indicates acute phase infection of Hepatitis A virus in the subject.

4. The method of claim 3, wherein the antibodies are in a biological sample from the subject.

5. A method of enhancing immunoreactivity of a synthetic peptide to an Igm antibody directed against Hepatitis A Virus, comprising synthesizing the peptide with one or more glutamine molecules at the carboxyl terminal of the peptide, wherein the carboxyl terminal glutamine enhances immunoreactivity of the peptide to an Igm antibody directed against Hepatitis A Virus.

6. The method of claim 5, where in the peptide is at least about nine amino acid residues in length to about 35 amino acid residues in length.

7. The method of claim 6, wherein the peptide has a primary structure not identical to a peptide of HAV.

* * * * *

UNITED STATES PATENT AND TRADEMARK OFFICE
CERTIFICATE OF CORRECTION

| | | |
|---|---|---|
| PATENT NO. | : 7,223,535 B2 | Page 1 of 1 |
| APPLICATION NO. | : 10/738443 | |
| DATED | : May 29, 2007 | |
| INVENTOR(S) | : Howard A. Fields et al. | |

It is certified that error appears in the above-identified patent and that said Letters Patent is hereby corrected as shown below:

Column 15, line 16, replace "hydroxylprotecting" with -- hydroxyl protecting --

Signed and Sealed this

Sixteenth Day of October, 2007

JON W. DUDAS
*Director of the United States Patent and Trademark Office*

SEQUENCE LISTING

<160> NUMBER OF SEQ ID NOS: 94

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 1

Gly Leu Asp His Ile Leu Ser Leu Ala Asp Ile Glu Glu Glu Gln Met
 1               5                  10                  15

Ile Gln Ser Val Gln
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 2

```
Asp Arg Thr Ala Val Thr Gly Ala Ser Tyr Phe Thr Ser Val Asp Gln
 1               5                  10                  15

Ser Ser Val His Gln
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 3

Glu Val Gly Ser His Gln Val Glu Pro Leu Arg Thr Ser Val Asp Lys
 1               5                  10                  15

Pro Gly Ser Lys Gln
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 4

Glu Pro Leu Arg Thr Ser Val Asp Lys Pro Gly Ser Lys Lys Thr Gln
 1               5                  10                  15

Gly Glu Lys Phe Gln
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 5

Asp Lys Pro Gly Ser Lys Lys Thr Gln Gly Glu Lys Phe Phe Leu Ile
 1               5                  10                  15

His Ser Ala Asp Gln
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP2 and VP4 Peptides

<400> SEQUENCE: 6

Leu Tyr Asn Glu Gln Phe Ala Val Gln Gly Leu Leu Arg Tyr His Thr
 1               5                  10                  15

Tyr Ala Arg Phe Gln
            20

<210> SEQ ID NO 7
<211> LENGTH: 20
<212> TYPE: PRT
<213> ORGANISM: Artificial Sequence
```

-continued

<220> FEATURE:
<223> OTHER INFORMATION: Description of Artificial Sequence:Synthetic
HAV VP2 and VP4 Peptides

<400> SEQUENCE: 7

His Thr Tyr Ala Arg Phe Gly Ile Glu Ile Gln Val Gln Ile Asn Pro
1 5 10 15

Thr Pro Phe Gln
20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence:Synthetic
HAV VP2 and VP4 Peptides

<400> SEQUENCE: 8

Ile Asn Pro Thr Pro Phe Gln Gln Gly Gly Leu Ile Cys Ala Met Val
1 5 10 15

Pro Gly Asp Gln
20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP2 and VP4 Peptides

<400> SEQUENCE: 9

His Phe Lys Asp Pro Gln Tyr Pro Val Trp Glu Leu Thr Ile Arg Val
1 5 10 15

Trp Ser Glu Leu Gln
20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP2 and VP4 Peptides

<400> SEQUENCE: 10

Asn Ile Gly Thr Gly Thr Ser Ala Tyr Thr Ser Leu Asn Val Leu Ala
1 5 10 15

Arg Phe Thr Asp Gln
20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP3 Peptide

<400> SEQUENCE: 11

Ser Asp Pro Ser Gln Gly Gly Gly Ile Lys Ile Thr His Phe Thr Thr
1 5 10 15

Trp Thr Ser Ile Gln
20

```
<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 12

Gly Gly Ile Lys Ile Thr His Phe Thr Thr Trp Thr Ser Ile Pro Thr
  1               5                  10                  15

Leu Ala Ala Gln
             20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 13

Gln Phe Pro Phe Asn Ala Ser Asp Ser Val Gly Gln Gln Ile Lys Val
  1               5                  10                  15

Ile Pro Val Asp Gln
             20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 14

Phe Asn Ala Ser Asp Ser Val Gly Gln Gln Ile Lys Val Ile Pro Val
  1               5                  10                  15

Asp Pro Tyr Phe Gln
             20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 15

Ser Asp Ser Val Gly Gln Gln Ile Lys Val Ile Pro Val Asp Pro Tyr
  1               5                  10                  15

Phe Phe Gln Met Gln
             20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 16
```

```
Ile Lys Val Ile Pro Val Asp Pro Tyr Phe Phe Gln Met Thr Asn Thr
  1               5                  10                  15

Asn Pro Asp Gln Gln
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 17

Lys Cys Ile Thr Ala Leu Ala Ser Ile Cys Gln Met Phe Cys Phe Trp
  1               5                  10                  15

Arg Gly Asp Leu Gln
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 18

Phe Trp Arg Gly Asp Leu Val Phe Asp Phe Gln Val Phe Pro Thr Lys
  1               5                  10                  15

Tyr His Ser Gly Gln
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 19

Phe Asp Phe Gln Val Phe Pro Thr Lys Tyr His Ser Gly Arg Leu Leu
  1               5                  10                  15

Phe Cys Phe Val Gln
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 20

Phe Pro Thr Lys Tyr His Ser Gly Arg Leu Leu Phe Cys Phe Val Pro
  1               5                  10                  15

Gly Asn Glu Leu Gln
            20

<210> SEQ ID NO 21
<211> LENGTH: 21
<212> TYPE: PRT
```

```
<213> ORGANISM: Artificial Sequence
<220> FEATURE:
<223> OTHER INFORMATION: Description of Artificial Sequence:Synthetic
      HAV VP3  Peptide

<400> SEQUENCE: 21

Gly Ile Thr Leu Lys Gln Ala Thr Thr Ala Pro Cys Ala Val Met Asp
 1               5                  10                  15

Ile Thr Gly Val Gln
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP3  Peptide

<400> SEQUENCE: 22

Val Ala Ser His Val Arg Val Asn Val Tyr Leu Ser Ala Ile Asn Leu
 1               5                  10                  15

Glu Cys Phe Ala Gln
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 23

Thr Thr Val Ser Thr Glu Gln Asn Val Pro Asp Pro Gln Val Gly Ile
 1               5                  10                  15

Thr Thr Met Lys Gln
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 24

Gln Asn Val Pro Asp Pro Gln Val Gly Ile Thr Thr Met Lys Asp Leu
 1               5                  10                  15

Lys Gly Lys Ala Gln
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 25

Asn Arg Gly Lys Met Asp Val Ser Gly Val Gln Ala Pro Val Gly Ala
 1               5                  10                  15

Ile Thr Thr Ile Gln
```

```
<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 26

Ile Thr Thr Ile Glu Asp Pro Val Leu Ala Lys Lys Val Pro Glu Thr
 1               5                  10                  15

Phe Pro Glu Leu Gln
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 27

Glu Asp Pro Val Leu Ala Lys Lys Val Pro Glu Thr Phe Pro Glu Leu
 1               5                  10                  15

Lys Pro Gly Glu Gln
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 28

Ala Lys Lys Val Pro Glu Thr Phe Pro Glu Leu Lys Pro Gly Glu Ser
 1               5                  10                  15

Arg His Thr Ser Gln
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 29

Phe Pro Glu Leu Lys Pro Gly Glu Ser Arg His Thr Ser Asp His Met
 1               5                  10                  15

Ser Ile Tyr Lys Gln
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide
```

```
<400> SEQUENCE: 30

Asp His Met Ser Ile Tyr Lys Phe Met Gly Arg Ser His Phe Leu Cys
  1               5                  10                  15

Thr Phe Thr Phe Gln
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 31

His Phe Leu Cys Thr Phe Thr Phe Asn Ser Asn Asn Lys Glu Tyr Thr
  1               5                  10                  15

Phe Pro Ile Thr Gln
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 32

Thr Pro Val Gly Leu Ala Val Asp Thr Pro Trp Val Glu Lys Glu Ser
  1               5                  10                  15

Ala Leu Ser Ile Gln
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 33

Leu Ser Phe Ser Cys Tyr Leu Ser Val Thr Glu Gln Ser Glu Phe Tyr
  1               5                  10                  15

Phe Pro Arg Ala Gln
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV VP1 Peptide

<400> SEQUENCE: 34

Ser Val Thr Glu Gln Ser Glu Phe Tyr Phe Pro Arg Ala Pro Leu Asn
  1               5                  10                  15

Ser Asn Ala Met Gln
            20

<210> SEQ ID NO 35
<211> LENGTH: 21
```

-continued

<212> TYPE: PRT
<213> ORGANISM: Artificial Sequence
<220> FEATURE:
<223> OTHER INFORMATION: Description of Artificial Sequence:Synthetic
HAV VP1 Peptide

<400> SEQUENCE: 35

Pro Leu Asn Ser Asn Ala Met Leu Ser Thr Glu Ser Met Met Ser Arg
1 5 10 15

Ile Ala Ala Gly Gln
20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP1 Peptide

<400> SEQUENCE: 36

Met Ser Arg Ile Ala Ala Gly Asp Leu Glu Ser Ser Val Asp Asp Pro
1 5 10 15

Arg Ser Glu Glu Gln
20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP1 Peptide

<400> SEQUENCE: 37

Ala Gly Asp Leu Glu Ser Ser Val Asp Asp Pro Arg Ser Glu Glu Asp
1 5 10 15

Lys Arg Phe Glu Gln
20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence:Synthetic
HAV VP1 Peptide

<400> SEQUENCE: 38

Val Asp Asp Pro Arg Ser Glu Glu Asp Lys Arg Phe Glu Ser His Ile
1 5 10 15

Glu Cys Arg Lys Gln
20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence:Synthetic
HAV P2A Peptide

<400> SEQUENCE: 39

Ser His Ile Glu Cys Arg Lys Pro Tyr Lys Glu Leu Arg Leu Glu Val
1 5 10 15

-continued

```
Gly Lys Gln Arg Gln
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 40

Pro Tyr Lys Glu Leu Arg Leu Glu Val Gly Lys Gln Arg Leu Lys Tyr
 1               5                  10                  15

Ala Gln Glu Glu Gln
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 41

Gln Arg Leu Lys Tyr Ala Gln Glu Glu Leu Ser Asn Glu Val Leu Pro
 1               5                  10                  15

Pro Pro Arg Lys Gln
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 42

Val Leu Pro Pro Pro Arg Lys Met Lys Gly Leu Phe Ser Gln Ala Lys
 1               5                  10                  15

Ile Ser Leu Phe Gln
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 43

Phe Ser Gln Ala Lys Ile Ser Leu Phe Tyr Thr Glu Glu His Glu Ile
 1               5                  10                  15

Met Lys Phe Ser Gln
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide
```

```
<400> SEQUENCE: 44

Lys Val Asn Phe Pro His Gly Met Leu Asp Leu Glu Glu Ile Ala Ala
  1               5                  10                  15
Asn Ser Lys Asp Gln
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 45

Asp Leu Glu Glu Ile Ala Ala Asn Ser Lys Asp Phe Pro Asn Met Ser
  1               5                  10                  15
Glu Thr Asp Leu Gln
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 46

Lys Ile Asn Leu Ala Asp Arg Met Leu Gly Leu Ser Gly Val Gln Glu
  1               5                  10                  15
Ile Lys Glu Gln
            20

<210> SEQ ID NO 47
<211> LENGTH: 26
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 47

Gln Arg Leu Lys Tyr Ala Gln Glu Glu Leu Ser Asn Glu Val Leu Pro
  1               5                  10                  15
Pro Pro Arg Lys Met Lys Gly Leu Phe Gln
            20                  25

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence:Synthetic
      HAV P2A Peptide

<400> SEQUENCE: 48

Trp Leu Asn Pro Lys Lys Ile Asn Leu Ala Asp Arg Met Leu Gly Leu
  1               5                  10                  15
Ser Gly Val Gln Glu Ile Lys Glu Gln
            20                  25

<210> SEQ ID NO 49
```

-continued

```
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2B Peptide

<400> SEQUENCE: 49

Val Ile Gln Gln Leu Asn Gln Asp Glu His Ser His Ile Ile Gly Leu
  1               5                  10                  15

Leu Arg Val Met Gln
             20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 50

Asn Ile Leu Lys Asp Asn Gln Gln Lys Ile Glu Lys Ala Ile Glu Glu
  1               5                  10                  15

Ala Asp Glu Phe Gln
             20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 51

Leu Gly Ser Ile Asn Gln Ala Met Val Thr Arg Cys Glu Pro Val Val
  1               5                  10                  15

Cys Tyr Leu Tyr Gln
             20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 52

Arg Cys Glu Pro Val Val Cys Tyr Leu Tyr Gly Lys Arg Gly Gly Gly
  1               5                  10                  15

Lys Ser Leu Thr Gln
             20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 53

Thr Lys Pro Val Ala Ser Asp Tyr Trp Asp Gly Tyr Ser Gly Gln Leu
  1               5                  10                  15
```

```
Val Cys Ile Ile Gln
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 54

Val Ser Gly Cys Pro Met Arg Leu Asn Met Ala Ser Leu Glu Glu Lys
  1               5                  10                  15

Gly Arg His Phe Gln
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 55

Leu Asn Met Ala Ser Leu Glu Glu Lys Gly Arg His Phe Ser Ser Pro
  1               5                  10                  15

Phe Ile Ile Ala Gln
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 56

Asn Pro Ser Pro Lys Thr Val Tyr Val Lys Glu Ala Ile Asp Arg Arg
  1               5                  10                  15

Leu His Phe Lys Gln
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 57

Val Lys Glu Ala Ile Asp Arg Arg Leu His Phe Lys Val Glu Val Lys
  1               5                  10                  15

Pro Ala Ser Phe Gln
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence:Synthetic
```

HAV P2C Peptide

<400> SEQUENCE: 58

Val Lys Pro Ala Ser Phe Phe Lys Asn Pro His Asn Asp Met Leu Asn
1               5                   10                  15

Val Asn Leu Ala Gln
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 59

Lys Asn Pro His Asn Asp Met Leu Asn Val Asn Leu Ala Lys Thr Asn
1               5                   10                  15

Asp Ala Ile Lys Gln
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 60

Leu Ala Lys Thr Asn Asp Ala Ile Lys Asp Met Ser Cys Val Asp Leu
1               5                   10                  15

Ile Met Asp Gly Gln
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence:Synthetic
      HAV P2C Peptide

<400> SEQUENCE: 61

Val Met Thr Val Glu Ile Arg Lys Gln Asn Met Thr Glu Phe Met Glu
1               5                   10                  15

Leu Trp Ser Gln
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3A Peptide

<400> SEQUENCE: 62

Ser Gln Gly Ile Ser Asp Asp Asp Asn Asp Ser Ala Val Ala Glu Phe
1               5                   10                  15

Phe Gln Ser Phe Gln
            20

-continued

```
<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3A Peptide

<400> SEQUENCE: 63

Asp Ser Ala Val Ala Glu Phe Phe Gln Ser Phe Pro Ser Gly Glu Pro
 1               5                  10                  15

Ser Asn Ser Lys Gln
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3A Peptide

<400> SEQUENCE: 64

Phe Gln Ser Phe Pro Ser Gly Glu Pro Ser Asn Ser Lys Leu Ser Gly
 1               5                  10                  15

Phe Phe Gln Ser Gln
            20

<210> SEQ ID NO 65
<211> LENGTH: 25
<212> TYPE: PRT
<213> ORGANISM: Artificial Sequence
<220> FEATURE:
<223> OTHER INFORMATION: Description of Artificial Sequence:Synthetic
      HAV P3A Peptide

<400> SEQUENCE: 65

Ser Ala Val Ala Glu Phe Phe Gln Ser Phe Pro Ser Gly Glu Pro Ser
 1               5                  10                  15

Asn Ser Lys Leu Ser Gly Phe Phe Gln
            20                  25

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence:Synthetic
      HAV P3B Peptide

<400> SEQUENCE: 66

His Gly Val Thr Lys Pro Lys Gln Val Ile Lys Leu Asp Ala Asp Pro
 1               5                  10                  15

Val Glu Ser Gln
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3C Peptide

<400> SEQUENCE: 67

Gly Leu Val Arg Lys Asn Leu Val Gln Phe Gly Val Gly Glu Lys Asn
```

-continued

```
  1               5                   10                  15

Gly Cys Val Arg Gln
             20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3C Peptide

<400> SEQUENCE: 68

Asp Val Val Leu Met Lys Val Pro Thr Ile Pro Lys Phe Arg Asp Ile
  1               5                   10                  15

Thr Gln His Phe Gln
             20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3C Peptide

<400> SEQUENCE: 69

Met Glu Glu Lys Ala Thr Tyr Val His Lys Lys Asn Asp Gly Thr Thr
  1               5                   10                  15

Val Asp Leu Thr Gln
             20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3C Peptide

<400> SEQUENCE: 70

Lys Asn Asp Gly Thr Thr Val Asp Leu Thr Val Asp Gln Ala Trp Arg
  1               5                   10                  15

Gly Lys Gly Glu Gln
             20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence:Synthetic
      HAV P3C Peptide

<400> SEQUENCE: 71

Arg Gly Lys Gly Glu Gly Leu Pro Gly Met Cys Gly Gly Ala Leu Val
  1               5                   10                  15

Ser Ser Asn Gln
             20

<210> SEQ ID NO 72
<211> LENGTH: 20
<212> TYPE: PRT
<213> ORGANISM: Artificial Sequence
<220> FEATURE:
```

```
<223> OTHER INFORMATION: Description of Artificial Sequence:Synthetic
      HAV P3C Peptide

<400> SEQUENCE: 72

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence:Synthetic
     HAV P3D Peptide

<400> SEQUENCE: 77

Cys Pro Lys Asp Glu Leu Arg Pro Leu Glu Lys Val Leu Glu Ser Lys
 1               5                  10                  15

Thr Arg Ala Ile Gln
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence:Synthetic HAV P3D Peptide

<400> SEQUENCE: 78

Ser Lys Thr Arg Ala Ile Asp Ala Cys Pro Leu Asp Tyr Ser Ile Leu
1 5 10 15

Cys Arg Met Tyr Gln
20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence:Synthetic HAV P3D Peptide

<400> SEQUENCE: 79

Arg Met Tyr Trp Gly Pro Ala Ile Ser Tyr Phe His Leu Asn Pro Gly
1 5 10 15

Phe His Thr Gly Gln
20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence:Synthetic HAV P3D Peptide

<400> SEQUENCE: 80

Lys Thr Met Ile Arg Phe Gly Asp Val Gly Leu Asp Leu Asp Phe Ser
1 5 10 15

Ala Phe Asp Ala Gln
20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence:Synthetic HAV P3D Peptide

<400> SEQUENCE: 81

```
Asp Leu Asp Phe Ser Ala Phe Asp Ala Ser Leu Ser Pro Phe Met Ile
 1               5                  10                  15

Arg Glu Ala Gly Gln
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3D Peptide

<400> SEQUENCE: 82

Ile Asn Asn Val Asn Leu Tyr Tyr Val Phe Ser Lys Ile Phe Gly Lys
 1               5                  10                  15

Ser Pro Val Phe Gln
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3D Peptide

<400> SEQUENCE: 83

Gly Gln Lys Ile Val Asp Glu Phe Lys Lys Leu Gly Met Thr Ala Thr
 1               5                  10                  15

Ser Ala Asp Lys Gln
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3D Peptide

<400> SEQUENCE: 84

Leu Gly Met Thr Ala Thr Ser Ala Asp Lys Asn Val Pro Gln Leu Lys
 1               5                  10                  15

Pro Val Ser Glu Gln
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence:Synthetic
      HAV P3D Peptide

<400> SEQUENCE: 85

Pro Gln Leu Lys Pro Val Ser Glu Leu Thr Phe Leu Lys Arg Ser Phe
 1               5                  10                  15

Asn Leu Val Glu Gln
            20

<210> SEQ ID NO 86
<211> LENGTH: 20
<212> TYPE: PRT
<213> ORGANISM: Artificial Sequence
```

-continued

```
<220> FEATURE:
<223> OTHER INFORMATION: Description of Artificial Sequence:Synthetic
      HAV P3D Peptide

<400> SEQUENCE: 86

Ser Glu Lys Thr Ile Trp Ser Leu Ile Ala Trp Gln Arg Ser Asn Ala
1

```
<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 91

Gly Gly Gly Gly Gly Gly Gly Gly Gly Gly Gly Gly Gly Gly Gly Gly
 1               5                   10                  15

Gly Gly Gly Gly
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 92

Gly Gly Gly Gly Gly Gly Gly Gly Gly Gly Gly Gly Gly Gly Gly Gly
 1               5                   10                  15

Gly Gly Gly Gly Gln
            20

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 93

Gly Gly Gly Gly Gly Ala Ala Ala Ala Ala Gly Gly Gly Gly Gly Ala
 1               5                   10                  15

Ala Ala Ala Ala
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 94

Gly Gly Gly Gly Gly Ala Ala Ala Ala Ala Gly Gly Gly Gly Gly Ala
 1               5                   10                  15

Ala Ala Ala Ala Gln
            20
```